(12) United States Patent
Karlsson et al.

(10) Patent No.: US 9,316,636 B2
(45) Date of Patent: Apr. 19, 2016

(54) METHOD AND SYSTEM FOR DETERMINATION OF MOLECULAR INTERACTION PARAMETERS

(71) Applicant: GE HEALTHCARE BIO-SCIENCES AB, Uppsala (SE)

(72) Inventors: Robert Karlsson, Uppsala (SE); Karl Andersson, Uppsala (SE); Christina Wass, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 0 days.

(21) Appl. No.: 13/659,960

(22) Filed: Oct. 25, 2012

(65) Prior Publication Data

US 2013/0065251 A1    Mar. 14, 2013

Related U.S. Application Data

(63) Continuation of application No. 13/038,432, filed on Mar. 2, 2011, now Pat. No. 8,321,152, which is a continuation of application No. 12/105,355, filed on Apr. 18, 2008, now Pat. No. 7,925,448, which is a continuation of application No. 10/861,098, filed on Jun. 4, 2004, now Pat. No. 7,373,255.

(60) Provisional application No. 60/526,364, filed on Dec. 1, 2003, provisional application No. 60/477,909, filed on Jun. 12, 2003.

(30) Foreign Application Priority Data

Jun. 6, 2003   (SE) .................................. 0301639
Dec. 1, 2003   (SE) .................................. 0303214

(51) Int. Cl.
| | |
|---|---|
| G06F 7/00 | (2006.01) |
| G01N 33/53 | (2006.01) |
| G01N 33/543 | (2006.01) |
| B01L 3/00 | (2006.01) |
| G01N 35/08 | (2006.01) |

(52) U.S. Cl.
CPC .............. *G01N 33/53* (2013.01); *G01N 33/543* (2013.01); *B01L 3/5027* (2013.01); *G01N 35/08* (2013.01); *Y10S 707/99943* (2013.01)

(58) Field of Classification Search
None
See application file for complete search history.

(56) References Cited

U.S. PATENT DOCUMENTS

| | | | |
|---|---|---|---|
| 4,988,447 A | 1/1991 | Hellinger | |
| 5,313,264 A * | 5/1994 | Ivarsson et al. ................. 356/73 |
| 5,753,518 A | 5/1998 | Karlsson | |
| 6,143,574 A | 11/2000 | Karlsson et al. | |
| 6,318,157 B1 | 11/2001 | Corso et al. | |
| 6,589,798 B1 | 7/2003 | Lofas | |
| 2003/0143565 A1 | 7/2003 | Trutnau | |
| 2003/0159999 A1 * | 8/2003 | Oakey et al. .................. 210/695 |
| 2004/0005582 A1 | 1/2004 | Shipwash | |
| 2004/0109793 A1 * | 6/2004 | McNeely et al. ............. 422/100 |
| 2004/0152200 A1 * | 8/2004 | Deshmukh ..................... 436/86 |
| 2005/0131650 A1 | 6/2005 | Andersson et al. | |

FOREIGN PATENT DOCUMENTS

| | | |
|---|---|---|
| EP | 0 247 800 | 12/1987 |
| EP | 0 444 441 | 9/1991 |
| EP | 1 162 455 | 8/1994 |
| EP | 0 361 810 | 12/1994 |

OTHER PUBLICATIONS

"Binding Capacity and Regeneration," in Proceedings of the BIAsymposium, Edinburgh, UK, Sep. 2-4, 1998, p. 4.
Hall, D., et al., "Use of a Resonant Mirror Biosensor to Characterize the Interaction of Carboxypeptidase A with an Elicited Monoclonal Antibody," Analytical Biochemistry 44:152-160, 1997.
Myszka, D., et al., "Equilibrium Analysis of High Affinity Interactions Using Biacore," Analytical Biochemistry 265:326-330, 1998.
Schuck, P., et al., "Determination of Binding Constants by Equilibrium Titration with Circulating Sample in a Surface Plasmon Resonance Biosensor," Analytical Biochemistry 265:79-91, 1998.
Shank-Retzlaff, M., et al., "Analyte Gradient-Surface Plasmon Resonance: A One-Step Method for Determining Kinetic Rates and Macromolecular Binding Affinities," Analytical Chemistry 72:(17):4212-4220, Sep. 1, 2000.
Willumsen, B., et al., "Flow Injection Renewable Surface Immunoassay for Real Time Monitoring of Biospecific Interactions," Analytical Chemistry 69(17):3482-3489, Sep. 1, 1997.

* cited by examiner

*Primary Examiner* — Michael Borin
(74) *Attorney, Agent, or Firm* — Sutherland Asbill & Brennan LLP

(57) ABSTRACT

A method of determining kinetic parameters for a reversible molecular interaction between a ligand immobilized to a solid support surface and a binding partner to the ligand in solution, comprises sequentially, without intermediate regeneration or renewal of the immobilized ligand, flowing a plurality of fluid volumes containing different known concentrations of the binding partner over the solid support surface, monitoring the momentary amount of binding partner bound to the solid support surface related to time and solution concentration of binding partner and collecting the binding data, and determining the kinetic parameters by globally fitting a predetermined kinetic model for the interaction between the binding partner and the immobilized ligand to the collected binding data, which model allows for mass transport limitation at the solid support surface. An analytical system for carrying out the method, a computer program, a computer program product and a computer system for performing the method are also disclosed.

9 Claims, 12 Drawing Sheets

METHOD AND SYSTEM FOR DETERMINATION OF MOLECULAR INTERACTION PARAMETERS

CROSS-REFERENCE TO RELATED APPLICATIONS

This application claims the benefit of U.S. Provisional Patent Application No. 60/477,909, filed Jun. 12, 2003 and U.S. Provisional Patent Application No. 60/526,364, filed Dec. 1, 2003; and also claims priority to Swedish Patent Application No. 0301639-1, filed Jun. 6, 2003 and Swedish Patent Application No. 0303214-1, filed Dec. 1, 2003; all of these applications are incorporated herein by reference in their entireties.

BACKGROUND OF THE INVENTION

1. Field of the Invention

The present invention relates to the determination of kinetic parameters for molecular interactions, and more particularly to a method for determining kinetic parameters for the interaction between a molecule immobilized to a solid support surface and a binding partner to the molecule in solution. The invention also relates to an analytical system, a computer program product and a computer system for performing the method.

2. Description of the Related Art

Analytical sensor systems that can monitor interactions between molecules, such as biomolecules, in real time are gaining increasing interest. These sensor systems, usually referred to as interaction analysis sensor systems or biospecific interaction analysis sensor systems, are often based on optical biosensors and affinity analysis and offer a rapid way to determine in real time inter alia equilibrium and rate constants without the need to label the interacting molecules. They have been used in the study of a variety of biomolecules, including proteins, nucleic acids, lipids and carbohydrates. In these systems, a sensor surface having one of the molecular reactants immobilized thereto is contacted with a solution containing the other reactant, either by providing a flow of the solution past the sensor surface, or in a cuvette or the like, and binding interactions at the surface are detected.

Conventionally, to determine, for example, association and dissociation rate constants ($k_a$ and $k_d$, respectively) for the interaction between two interacting molecules, one of the molecules, often referred to as the ligand, is immobilized to a sensor surface and the other molecule, often referred to as the analyte, is provided in solution at several different known concentrations. Each concentration, or sample, of the analyte is then contacted with the sensor surface, either in a laminar flow past the sensor surface, or in a cuvette or the like, to permit association of the analyte to the sensor surface. After a sample has been brought to contact the sensor surface, the surface is contacted with a solution free from analyte, usually buffer, to permit dissociation of the analyte from the immobilized ligand. During these association and dissociation phases, the amount of binding of analyte to the surface is continuously detected and the binding data is collected. Before contacting the sensor surface with sample of a new analyte concentration, the ligand surface is restored or "regenerated" by treating the surface with a regeneration solution capable of removing any bound analyte while not destroying the ligand. In that way, all the different samples will contact essentially one and the same ligand surface as far as ligand density is concerned. The association and dissociation rate constants can then be obtained from the collected binding data by fitting the data to mathematical descriptions of interaction models in the form of differential equations. Usually, the binding data for all the samples are used in the same fit, a procedure referred to as global fitting. From the determined association and dissociation rate constants $k_a$ and $k_d$, the equilibrium constant, $K_D$, and the affinity constant $K_A$ ($K_A=1/K_D$) of the interaction can in turn be calculated. Alternatively, provided that the interaction reaches steady state during the association phase, the equilibrium constant can be directly obtained from the binding data without fitting.

Problems may arise, however, when the ligands are covalently immobilized to the sensor surface and suitable regeneration conditions are difficult to find. Renewed binding of the ligand via an immobilized capture agent before the contacting with each new analyte concentration could then be an alternative, but has the disadvantage of consuming large amounts of ligand for the determination.

Determination of equilibrium constants by a titration procedure without the requirement for regeneration of the immobilized ligands is described by Schuck, P., et al. (1998) *Anal. Biochem.* 265, 79-91. The sample is continuously circulated in a closed loop over two sensor spots of a commercial surface plasmon resonance biosensor. One of the sensor spots is functionalized with an immobilized ligand for a soluble analyte in the sample, and the other sensor spot serves as a reference surface. A binding isotherm for the interacting molecules is obtained by stepwise equilibrium titration of the analyte into the circulating loop, i.e., the sensor spots are sequentially contacted with stepwise increased concentrations of analyte until equilibrium is attained for each concentration. This equilibrium titration is said to be especially useful for the determination of binding constants in high-affinity systems since it eliminates the need for interpretation of binding kinetics and thereby problems that may arise from mass transport limitations.

A similar stepwise equilibrium titration procedure is described for a cuvette-based biosensor design in Hall, D. R., and Winzor, D. J. (1997) *Anal. Biochem.* 244, 152-160.

Also Myszka, D. G., et al. (1998) Anal. Biochem. 265, 326-330 discloses equilibrium analysis of high affinity interactions using a surface plasmon resonance-based biosensor. In this approach, the time available to collect association phase data is increased by placing the analyte directly into the running buffer. Complete equilibrium binding profiles were generated without a regeneration step by changing the concentration of analyte and allowing the surface reactions to reequilibrate. Analyte concentrations were also decreased to demonstrate that the binding reactions were fully reversible. In this way, equilibrium dissociation constants for very high affinity interactions could be determined.

Shank-Retzlaff, M. L., and Sligar, S. G. (2000) *Anal. Chem.* 72, 4212-4220 describes a one-step method for determining kinetic rates and equilibrium binding affinities by a technique called analyte-gradient surface plasmon resonance SPR (AG-SPR) which eliminates the need for surface regeneration. A gradient of analyte is passed over the sensor surface under continuous-flow conditions so that the concentration of analyte increases linearly with time. The rate at which analyte binds to immobilized ligands on the sensor surface is monitored by monitoring the change in the surface plasmon resonance as the analyte concentration increases. Kinetic rates are determined by fitting the data to a two-compartment model for the molecular interaction which permits use also for systems under mass transport limitations.

Titration procedures to determine binding capacity and regeneration conditions have been proposed by Karlsson, R., et al., Biasymposium 1998, Edinburgh 2-4 Sep. 1998, 5th Biasymposium in Japan, Tokyo, Nov. 5-6, 1998.

US-A1-2003/014365 discloses a method for determining interaction parameters, including rate constants, between an analyte and a ligand immobilized to a sensor surface, where a measurement can be performed several times in succession, e.g., in a cuvette, with a stepwise modification of the analyte concentration each time. The measurements need not be completed to equilibrium but can be interrupted earlier and the concentration of the analyte can be raised or lowered. Separate fitting of the binding curve part corresponding to each analyte concentration is used to determine respective initial binding rates, from which the association and dissociation rate constants for the interaction are then determined.

Thus, while titration procedures in combination with biosensors and affinity analysis are known per se in the art for determining equilibrium binding affinities, the use of multiple titrations to determine kinetic rate constants seems to be disclosed only in the above-mentioned publications Shank-Retzlaff, M. L., and Sligar, S. G. (2000), and US-A1-2003/014365. The method according to Shank-Retzlaff, M. L., and Sligar, S. G. (2000) suffers from the limitation that it requires the use of a continuous gradient of the analyte. The method of US-A1-2003/014365, on the other hand, is disadvantageous in that initial binding rates are frequently lower than the kinetic binding rate due to transport limitations, making initial binding rates unreliable for kinetic analysis. Further, this type of evaluation restricts the injection order of analyte concentrations.

From the prior art it may therefore be concluded that for determining kinetic rates for molecular interactions using systems based on biosensors and affinity analysis, it is necessary to regenerate the immobilized ligand prior to contacting the sensor surface with a different concentration of analyte to thereby present essentially one and the same ligand surface to each analyte concentration, unless (i) a continuous gradient of the analyte is used, or (ii) initial binding rates are determined in systems free from mass transport limitations.

It is an object of the present invention to provide a sensor-based method for determining chemical interaction parameters, including kinetic rate constants, by stepwise titration, which method obviates regeneration procedures while permitting measurements under mass transport limitation.

BRIEF SUMMARY OF THE INVENTION

According to the present invention, it has surprisingly been found that the above and other objects and advantages can be achieved by an affinity sensor-based method for determining chemical interaction parameters, which method comprises performing, in one and the same experimental cycle, stepwise changes of the analyte concentration without intermediate regeneration of the sensor surface, and determining the interaction parameters using global analysis of the whole set of detected binding data with regard to a kinetic model for the molecular interaction that allows for mass transport limitation, such as, e.g., the afore-mentioned two-compartment model. In this method, kinetic data can thus be obtained in spite of mass transport limitations and the different analyte concentrations may be used in any order.

Therefore, in one aspect, the present invention provides a method of determining kinetic parameters for a reversible molecular interaction between a ligand immobilized to a sensor surface and a binding partner (analyte) to the ligand in solution, comprising the steps of:

a) sequentially, without intermediate regeneration or renewal of the immobilized ligand, flowing a plurality of fluid volumes containing different known concentrations of the binding partner over the solid support surface to permit association of binding partner to the immobilized ligand, b) flowing over the solid support surface a fluid volume free from binding partner to permit dissociation of binding partner from the ligand, c) monitoring during steps a) and b) the momentary amount of binding partner bound to the solid support surface related to time and solution concentration of binding partner and collecting the binding data, and d) determining the kinetic parameters by fitting, preferably globally, a predetermined kinetic model for the interaction between the binding partner and the immobilized ligand to the collected binding data, which model allows for mass transport limitation at the solid support surface.

Preferably, the flowing of a plurality of different known concentrations of binding partner in step a) starts with the concentration of zero binding partner and continues with concentrations above zero.

In a variant method, the different concentrations of binding partner are obtained by generating a gradient of the binding partner and intersecting segments of the gradient with segments of a fluid free from binding partner.

In another aspect, the present invention therefore provides a method of determining kinetic parameters for a reversible molecular interaction between a ligand immobilized to a sensor surface and a binding partner (analyte) to the ligand in solution, comprising the steps of:

a) sequentially, without intermediate regeneration or renewal of the immobilized ligand, flowing a plurality of fluid volumes containing different concentrations of the binding partner over the solid support surface to permit association of binding partner to the immobilized ligand, wherein the fluid volumes containing binding partner are discrete segments of a concentration gradient of the binding partner separated by segments of fluid free from binding partner, b) monitoring during step a) the momentary amount of binding partner bound to the solid support surface related to time and solution concentration of binding partner and collecting the binding data, and c) determining the kinetic parameters by fitting a predetermined kinetic model for the interaction between the binding partner and the immobilized ligand to the collected binding data.

Preferably, the model allows for mass transport limitation at the solid support surface.

In the case that the concentrations of all the gradient segments are not known, the unknown concentrations may be estimated. This may, for example, be done by having the fitting in step d) include local fitting of concentrations.

The solid support surface is preferably a sensor surface, i.e., one which produces a detectable signal in response to a binding interaction at the surface.

The term "monitoring" as used herein means that detection is performed at at least a plurality of times during steps a) and b), preferably at a large number of times.

In another aspect, the present invention provides a method for determining the concentrations of binding partner in a plurality of binding partner-containing samples.

In still another aspect, the present invention provides a method for determining kinetic parameters for a plurality of different binding partners.

In another aspect, the present invention provides an analytical system for studying molecular interactions, which system comprises data processing means for performing at least one of the methods.

In yet another aspect, the present invention provides a computer program comprising program code means for performing at least one of the methods.

In still another aspect, the present invention provides a computer program product comprising program code means stored on a computer readable medium or carried on an electrical or optical signal for performing at least one of the methods.

In another aspect, the present invention provides a computer system containing a computer program comprising program code means for performing at least one of the methods.

Other advantages, novel features and objects of the invention will become apparent from the following detailed description of the invention when considered in conjunction with the accompanying drawings.

DETAILED DESCRIPTION OF THE INVENTION

Figure 1:
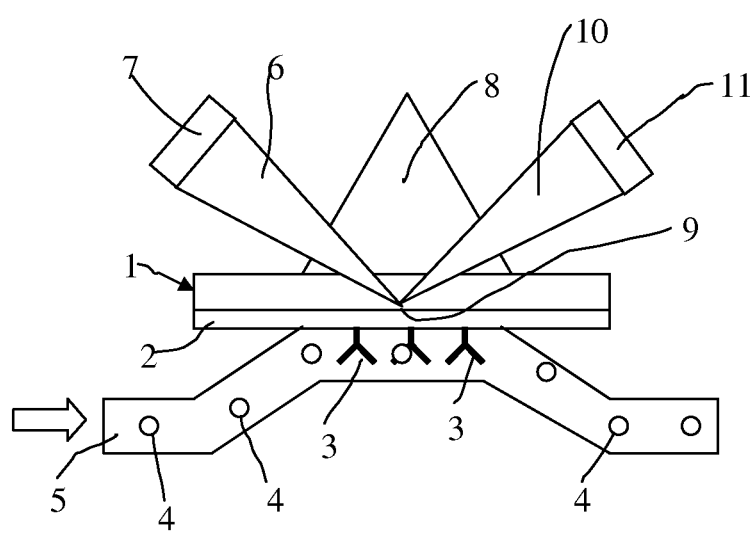
FIG. 1 is a schematic side view of a biosensor system based on surface plasmon resonance (SPR).

Unless defined otherwise, all technical and scientific terms used herein have the same meaning as commonly understood by a person skilled in the art related to this invention. Also, the singular forms "a", "an", and "the" are meant to include plural reference unless it is stated otherwise.

As mentioned above, the present invention relates to the determination of molecular interaction parameters, including kinetic rate constants, for the interaction between a molecule immobilized to a solid support surface and a binding partner to the molecule in solution by a novel titration type method, preferably in combination with sensor based technology to study the molecular interactions and present the results in real time, as the interactions progress. Before describing the present invention in more detail, however, the general context in which the invention is used will be described.

Chemical sensors or biosensors are typically based on label-free techniques, detecting a change in a property of a sensor surface, such as, e.g., mass, refractive index, or thickness for the immobilized layer, but there are also sensors relying on some kind of labelling. Typical sensor detection techniques include, but are not limited to, mass detection methods, such as optical, thermo-optical and piezoelectric or acoustic wave, (including, e.g., surface acoustic wave (SAW) and quartz crystal microbalance (QCM)) methods, and electrochemical methods, such as potentiometric, conductometric, amperometric and capacitance/impedance methods. With regard to optical detection methods, representative methods include those that detect mass surface concentration, such as reflection-optical methods, including both external and internal reflection methods, angle, wavelength, polarization, or phase resolved, for example evanescent wave ellipsometry and evanescent wave spectroscopy (EWS, or Internal Reflection Spectroscopy), both may include evanescent field enhancement via surface plasmon resonance (SPR), Brewster angle refractometry, critical angle refractometry, frustrated total reflection (FTR), scattered total internal reflection (STIR)—which may include scatter enhancing labels, optical wave guide sensors; external reflection imaging, evanescent wave-based imaging such as critical angle resolved imaging, Brewster angle resolved imaging, SPR-angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers, waveguide leaking mode spectroscopy, reflective interference spectroscopy (RIfS), transmission interferometry, holographic spectroscopy, and atomic force microscopy (AFR).

Commercially available biosensors include the BIACORE® system instruments, manufactured and marketed by Biacore AB, Uppsala, Sweden, which are based on surface plasmon resonance (SPR) and permit monitoring of surface binding interactions in real time between a bound ligand and an analyte of interest.

While in the detailed description and Examples that follow, the present invention is illustrated in the context of SPR spectroscopy, and more particularly the BIACORE® system, it is to be understood that the present invention is not limited to this detection method. Rather, any affinity-based detection method where an analyte binds to a ligand immobilized on a sensing surface may be employed, provided that a change at the sensing surface can be measured which is quantitatively indicative of binding of the analyte to the immobilized ligand thereon.

The phenomenon of SPR is well known, suffice it to say that SPR arises when light is reflected under certain conditions at the interface between two media of different refractive indices, and the interface is coated by a metal film, typically silver or gold. In the BIACORE® instruments, the media are the sample and the glass of a sensor chip which is contacted with the sample by a microfluidic flow system. The metal film is a thin layer of gold on the chip surface. SPR causes a reduction in the intensity of the reflected light at a specific angle of reflection. This angle of minimum reflected light intensity varies with the refractive index close to the surface on the side opposite from the reflected light, in the BIACORE® system the sample side.

A schematic illustration of the BIACORE® system is shown in FIG. 1. Sensor chip 1 has a gold film 2 supporting capturing molecules 3, e.g., antibodies, exposed to a sample flow with analytes 4 (e.g., an antigen) through a flow channel 5. Monochromatic p-polarised light 6 from a light source 7 (LED) is coupled by a prism 8 to the glass/metal interface 9 where the light is totally reflected. The intensity of the reflected light beam 10 is detected by an optical detection unit (photodetector array) 11.

A detailed discussion of the technical aspects of the BIACORE® instruments and the phenomenon of SPR may be found in U.S. Pat. No. 5,313,264. More detailed information on matrix coatings for biosensor sensing surfaces is given in, for example, U.S. Pat. Nos. 5,242,828 and 5,436,161. In addition, a detailed discussion of the technical aspects of the biosensor chips used in connection with the BIACORE® instruments may be found in U.S. Pat. No. 5,492,840. The full disclosures of the above-mentioned U.S. patents are incorporated by reference herein.

When molecules in the sample bind to the capturing molecules on the sensor chip surface, the concentration, and therefore the refractive index at the surface changes and an SPR response is detected. Plotting the response against time during the course of an interaction will provide a quantitative measure of the progress of the interaction. Such a plot is usually called a sensorgram. In the BIACORE® system, the SPR response values are expressed in resonance units (RU). One RU represents a change of 0.0001° in the angle of minimum reflected light intensity, which for most proteins and other biomolecules correspond to a change in concentration of about 1 pg/mm² on the sensor surface. As sample containing an analyte contacts the sensor surface, the ligand bound to the sensor surface interacts with the analyte in a step referred to as "association." This step is indicated on the sensorgram by an increase in RU as the sample is initially brought into contact with the sensor surface. Conversely, "dissociation" normally occurs when the sample flow is replaced by, for example, a buffer flow. This step is indicated on the sensorgram by a drop in RU over time as analyte dissociates from the surface-bound ligand.

Figure 2:
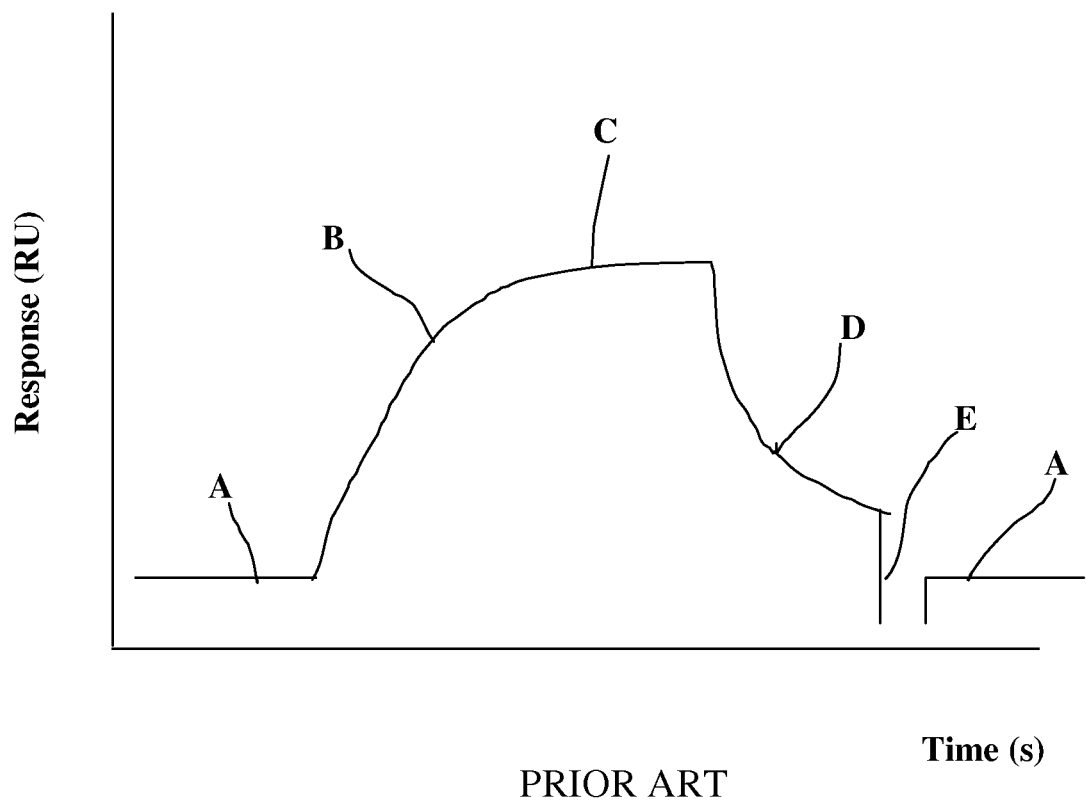
FIG. 2 is a representative sensorgram with a binding curve having association and dissociation phases.

A representative sensorgram (binding curve) for a reversible interaction at the sensor chip surface is presented in FIG. 2, the sensing surface having an immobilized capturing molecule, or ligand, for example an antibody, interacting with a binding partner therefor, or analyte, in a sample. (The detection curves, or sensorgrams, produced by biosensor systems based on other detection principles mentioned above will have a similar appearance.) The y-axis indicates the response (here in resonance units, RU) and the x-axis indicates the time (here in seconds). Initially, buffer is passed over the sensing surface giving the baseline response A in the sensorgram. During sample injection, an increase in signal is observed due to binding of the analyte. This part B of the binding curve is usually referred to as the "association phase". Eventually, a steady state condition is reached where the resonance signal plateaus at C (this state may, however, not always be achieved). At the end of sample injection, the sample is replaced with a continuous flow of buffer and a decrease in signal reflects the dissociation, or release, of analyte from the surface. This part D of the binding curve is usually referred to as the "dissociation phase". The analysis is ended by a regeneration step where a solution capable of removing bound analyte from the surface, while (ideally) maintaining the activity of the ligand, is injected over the sensor surface. This is indicated in part E of the sensorgram. Injection of buffer restores the baseline A and the surface is now ready for a new analysis.

From the profiles of the association and dissociation phases B and D, respectively, information regarding the binding and dissociation kinetics is obtained, and the height of the resonance signal represents surface concentration (i.e., the response resulting from an interaction is related to the change in mass concentration on the surface). This will now be explained in more detail below.

Assume a reversible reaction between an analyte A and a surface-bound (immobilized) capturing molecule, or ligand, B which is not diffusion or mass transfer limited and obeys pseudo first order kinetics:

$$A+B \Leftrightarrow AB$$

This interaction model (usually referred to as the Langmuir model), which assumes that the analyte (A) is both monovalent and homogenous, that the ligand (B) is homogenous, and that all binding events are independent, is in fact applicable in the vast majority of cases.

The rate of change in surface concentration of analyte A (=rate of change in concentration of formed complex AB) during analyte injection is the sum of the rates of the analyte A going on and off:

$$\frac{d[AB]}{dt} = k_a[A][B] - k_d[AB] \quad (1)$$

where [A] is the concentration of analyte A, [B] is the concentration of the ligand B, [AB] is the concentration of the reaction complex AB, $k_a$ is the association rate constant, and $k_d$ is the dissociation rate constant.

After a time t, the concentration of unbound ligand B at the surface is $[B_T]-[AB]$, where $[B_T]$ is the total, or maximum, concentration of ligand B. Insertion into Equation (1) gives:

$$\frac{d[AB]}{dt} = k_a[A]\{[B_T] - [AB]\} - k_d[AB] \quad (2)$$

In terms of detector response units (AB is detected), this can be expressed as $$\frac{dR}{dt} = k_a C(R_{max} - R) - k_d R \quad (3)$$

where R is the response at time t in resonance units (RU), C is the initial, or bulk, concentration of free analyte (A) in solution, and $R_{max}$ is the response (in RU) obtained if analyte (A) had bound to all ligand (B) on the surface. Rearrangement of Equation (3) gives:

$$\frac{dR}{dt} = k_a C R_{max} - (k_a C + k_d) R \quad (4)$$

where R is the response in resonance units (RU). In integrated form, the equation is:

$$R = \frac{k_a C R_{max}}{k_a C + k_d}(1 - e^{-(k_a C + k_d)t}) \quad (5)$$

Now, according to equation (4), if dR/dt is plotted against the bound analyte concentration R, the slope is $k_a C + k_d$ and the vertical intercept is $k_a R_{max} C$. If the bulk concentration C is known and $R_{max}$ has been determined (e.g., by saturating the surface with a large excess of analyte), the association rate constant $k_a$ and the dissociation rate constant $k_d$ can be calculated. A more convenient method is, however, fitting of the integrated function (5), or numerical calculation and fitting of the differential Equation (4), preferably by means of a computer program as will be described below.

The rate of dissociation can be expressed as:

$$\frac{dR}{dt} = -k_d R \quad (6)$$

and in integrated form:

$$R = R_0 \cdot e^{-k_d t} \quad (7)$$

where $R_0$ is the response at the beginning of the dissociation phase (when the buffer wash of the surface starts).

Equation (6) may be linearized:

$$\ln\left[\frac{R}{R_0}\right] = -k_d t \quad (8)$$

and a plot of $\ln[R/R_0]$ versus t will produce a straight line with the slope=$-k_d$. More conveniently, however, the dissociation rate constant $k_d$ is determined by fitting the exponential rate equation (7).

Affinity is expressed by the association constant $K_A = k_a/k_d$, or the dissociation constant (also referred to as the equilibrium constant) $K_D = k_d/k_a$.

The association constant $K_A$ may alternatively be determined from Equation (3), where $dR/dt=0$ at equilibrium, giving:

$$k_d R_{eq} = k_a C(R_{max} - R_{eq}) \quad (9)$$

where $R_{eq}$ is the detector response at equilibrium. Since $k_a/k_d = K_A$, insertion in Equation (9) and rearrangement gives:

$$\frac{R_{eq}}{C} = -K_A R_{eq} + K_A R_{max} \quad (10)$$

If binding reactions are performed at multiple concentrations, the data may either be fitted or $R_{eq}/C$ may be plotted versus $R_{eq}$ which gives the slope=$-K_A$. Such an equilibrium analysis may be performed when the rates of association and dissociation are too rapid to measure accurately.

To obtain reliable kinetic constants, the above described analysis is usually repeated for a number of different analyte concentrations and, suitably, also at least one other ligand density at the sensor surface.

Software for the analysis of kinetic and other biosensor data is commercially available. Thus, for example, evaluation of kinetic data produced by the BIACORE® instruments is usually performed with the dedicated BIAevaluation software (supplied by Biacore AB, Uppsala, Sweden) using numerical integration to calculate the differential rate equations and non-linear regression to fit the kinetic parameters by finding values for the variables that give the closest fit reducing the sum of squared residuals to a minimum. The residuals are the difference between the calculated and the experimental curve at each point, squared residuals being used to weight equally deviations above and below the experimental curve. The sum of squared residual is expressed by Equation (11):

$$S = \sum_1^n (r_f - r_x)^2 \quad (11)$$

where S is the sum of squared residuals, $r_f$ is the fitted value at a given point, and $r_x$ is the experimental value at the same point.

For example, for the molecular interaction described above, such software-assisted data analysis is performed by, after subtracting background noises, making an attempt to fit the above-mentioned simple 1:1 Langmuir binding model as expressed by Equations (5) and (7) above to the measurement data.

Usually the binding model is fitted simultaneously to multiple binding curves obtained with different analyte concentrations C (and/or with different levels of surface derivatization $R_{max}$). This is referred to as "global fitting", and based on the sensorgram data such global fitting establishes whether a single global $k_a$ or $k_d$ will provide a good fit to all the data. The results of the completed fit are presented to the operator graphically, displaying the fitted curves overlaid on the original sensorgram curves. The closeness of the fit is also presented by the chi-squared ($\chi^2$) value, a standard statistical measure. For a good fitting, the chi-squared value is in the same magnitude as the noise in $RU^2$. Optionally, "residual plots" are also provided which give a graphical indication of how the experimental data deviate from the fitted curve showing the difference between the experimental and fitted data for each curve. The operator then decides if the fit is good enough. If not, the sensorgram or sensorgrams exhibiting the poorest fit are excluded and the fitting procedure is run again with the reduced set of sensorgrams. This procedure is repeated until the fit is satisfactory.

Sometimes, the above-mentioned 1:1 binding reaction model will not be valid, which requires the data set to be reanalysed using one or more other reaction models. Such alternative models may include, for example, a one to one reaction influenced by mass transfer (mass transport), two parallel independent one to one reactions, two competing reactions, and a two state reaction. Parallel reactions can occur when the immobilized ligand is heterogeneous, whereas a heterogenous analyte may give rise to competing reactions. A two state reaction indicates a conformation change that gradually leads to a more stable complex between ligand and analyte. For differential rate equations reflecting these alternative reaction models, it may be referred to, for example, Karlsson, R., and Fält, A. (1997) *J. Immunol. Methods* 200, 121-133 (the disclosure of which is incorporated by reference herein). For a more comprehensive description of curve fitting with regard to the BIACORE® system, it may be referred to the BIAevaluation Software Handbook (Biacore AB, Uppsala, Sweden) (the disclosure of which is incorporated by reference herein).

As regards mass transport, transport effects will influence the kinetics of binding when the reaction rate is fast compared to the rate of transport. For a reaction where analyte (A) binds to immobilized ligand (B), binding with mass transport limitation may be represented by the reaction formula:

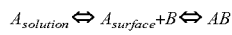

$$A_{solution} \Leftrightarrow A_{surface} + B \Leftrightarrow AB$$

The differential equations describing the binding interaction will therefore include terms for mass transfer of analyte to the surface. For a flow cell, a "two-compartment" model consisting of a set of coupled ordinary differential equations and described in inter alia Myszka, D. G., et al. (1998) *Biophys. J.* 75, 583-594, and Shank-Retzlaff, M. L., and Sligar, S.

G. (2000) supra (the relevant disclosures of which are incorporated by reference herein) is considered to give a reasonable description of the binding kinetics when the data are influenced by mass transport. In this model, the flow cell is assumed to be divided into two compartments, one in which the concentration of analyte is constant, and a second near the sensor surface where the analyte concentration depends on the mass transport rate, the surface density of ligand, and the reaction rate constants.

For the interaction of a monovalent analyte (A) reacting with an immobilized monovalent ligand (B), this model may be represented by the following two differential equations (12) and (13):

$$\frac{dA}{dt} = (-k_a A(B_T - AB) + k_d AB + k_t(C - A)) \quad (12)$$

$$\frac{dAB}{dt} = k_a A(B_T - AB) - k_d AB \quad (13)$$

where $k_t$ is the transport coefficient describing diffusive movement of analyte between the compartments, $B_T$ is the total ligand concentration, A is the bulk concentration of free analyte, C is the injection (i.e., initial) analyte concentration, AB is the concentration of complex AB (=surface density of bound analyte), and $k_a$ and $k_d$ are the association and dissociation rate constants, respectively.

It is understood that the use of this two-compartment model analyzing the kinetic globally will extend the range of reaction rates that can be determined with instruments like the BIACORE® and has also been incorporated in the above-mentioned BIAevaluation analysis software (available from Biacore AB, Uppsala, Sweden).

Theoretical interaction data for different interaction models may be simulated using a simulator, such as, e.g., the simulator which is built-in in the above-mentioned BIAevaluation analysis software. In this way, the effects of varying experimental parameters may be explored, thereby helping to determine which interaction conditions that may be crucial in distinguishing between alternative kinetic models.

The Invention

As mentioned above, determining kinetic parameters using, for example, a BIACORE® instrument, conventionally comprises monitoring the interaction of analyte with immobilized ligand for a plurality of different analyte concentrations with regeneration, or renewal, of the immobilized ligand before each measurement with a new analyte concentration. A kinetic model for the interaction is then fitted globally to the collected binding data, usually in the form of sensorgrams, to give the kinetic parameters.

According to the present invention, such a flow cell-based analysis for determining kinetic parameters may be substantially improved and speeded up by a titration type, or "sequential injection", procedure wherein the ligand-supporting surface is successively contacted, in one and the same analytical cycle, with the different analyte concentrations to produce a continuous sensorgram. A kinetic interaction model allowing for mass transport limitation, such as the two-compartment model mentioned above, is then fitted globally to the entire sensorgram to calculate the kinetic parameters. In addition to being considerably less time-consuming, this titration type method reduces the amount of experimental data to be evaluated and eliminates the risk of regeneration conditions destroying immobilized ligand.

The order of introducing the different analyte concentrations is not critical to the success of the inventive procedure. Rather, the analyte concentrations may, in fact, be introduced in any order. For example, the analyte concentrations may be successively increased, or successively decreased, or may alternately be higher and lower, etc. Further, the same concentration of analyte may be introduced repeatedly, if desired.

The injections of analyte, which preferably may be short, for a BIACORE® or similar instrument, e.g., in the order of 30-60 seconds, may be interrupted when an increased analyte concentration only leads to a marginally increased response. This may advantageously be effected using so-called adaptive software. The formed complex is then preferably allowed to dissociate for a longer period of time, e.g., from about 5 to 60 minutes in the context of a BIACORE® or similar instrument, to add adequate dissociation data for the kinetic evaluation. Such a dissociation period may, optionally, instead (or additionally) be performed between any two analyte injections in the cycle.

It is to be noted that the design of the above-mentioned BIACORE® instruments, for example, requires that each injection of analyte be followed by injection of running buffer, permitting partial dissociation of the bound analyte, before the next concentration of analyte is injected. It is understood that such alternating analyte-free liquid volumes, for example with about one minute intervals, will add dissociation data to the those obtained by the above-mentioned (preferably longer) dissociation period. Provided that sufficient dissociation data is obtained by these alternating injections of analyte-free fluid, the longer dissociation period may even be dispensed with. Intermediate buffer injections may, of course, also be used, even if a sensor instrument design as such permits sequential injections of analyte without buffer injections between them.

At least for some applications, it is preferred that the flow is substantially constant during the entire experimental cycle.

The sequential injection procedure may optionally be repeated at least once with the same or another sequence of analyte concentrations, and all the collected binding data may then be fitted simultaneously to the kinetic interaction model.

Optionally, the fluid volumes containing the different analyte concentrations may be different volume segments of a concentration gradient of the analyte. A method for the sequential injection of segments of a decreasing (or increasing) analyte gradient is described in our copending U.S. application entitled "Method and apparatus for characterization of interactions" (the disclosure of which is incorporated by reference herein).

In this "pulse injection" method, each injection consists of a series of short sample pulses, suitably 4 or 5 up to 40 pulses, preferably 15-30, more preferably about 20 pulses, generated by alternating flows of analyte-containing sample, and another liquid, such as buffer. Each pulse preferably has a volume of 1-40 µl, preferably 10-40 µl, more preferably 15-25 µl, suitably about 20 µl. The duration of the pulses, i.e., each segment of solution can be 8-20, preferably about 10-15, suitably 12 seconds long, and the flow rate for the sample liquid through the flow cell may be 50-200, preferably 80-120, suitably 100 µl/min.

In this way, information from several concentration levels will be generated through a single injection in that each pulse of the injection in principle constitutes one concentration. Optionally, some pulses during an injection may be discarded, whereby the discarded segments will not be passed through the sensor. Alternatively, some aliquot(s) of liquid can be discarded even before performing the alternating buffer injections to create the separated segments.

Depending on how the concentration gradient is prepared, the concentrations of all segments may or may not be known.

If all concentrations are known, the kinetic parameters may be determined by global fitting as described above. If, on the other hand, only the concentration of, say, an edge segment(s) is known, such as in the case of a "dispersion gradient", the fitting may have to include local fitting of the analyte concentrations.

If desired, binding data from one or more sequential experiments performed as described above may be combined with binding data from one or more conventional type single concentration experiments, and the combined data are then fitted to the kinetic interaction model. Thus, generally, the total data set that is globally fitted to the kinetic interaction model may comprise any combination of binding curves including one or more "sequential" binding curves and one or more single concentration binding curves.

Figure 3:
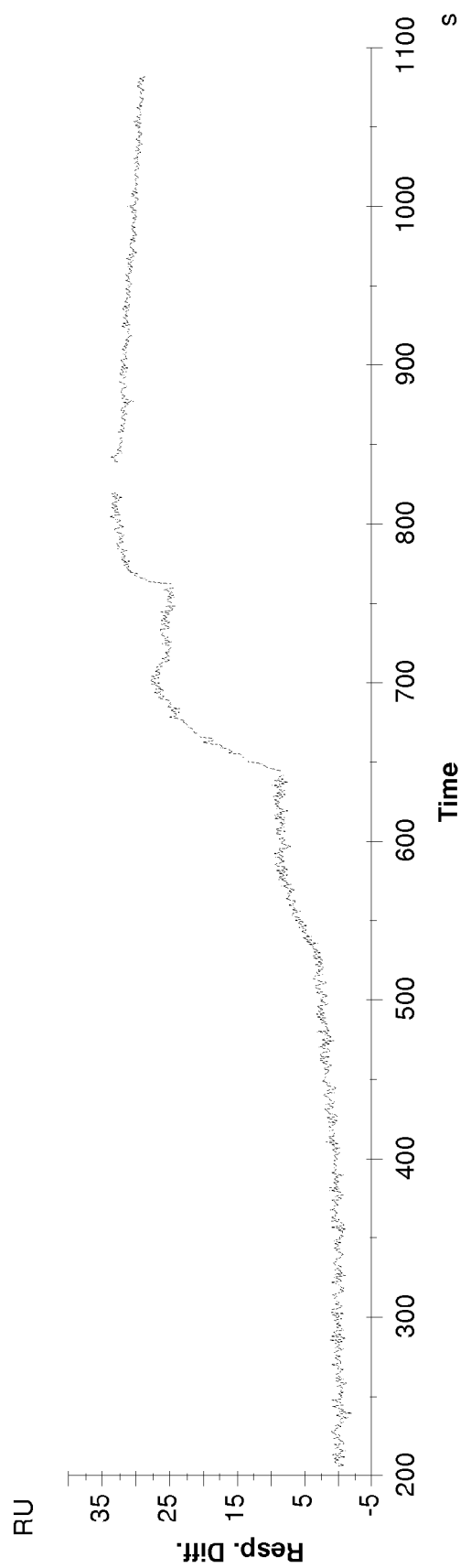
FIG. 3 is a representative sensorgram obtained by sequential injections of a kinase inhibitor (staurosporin) over a surface with immobilized kinase according to the method of the present invention.

To facilitate the understanding of the invention, reference is now made to FIG. 3 which shows an exemplary sensorgram (as obtained with the above-mentioned BIACORE® instrument) for a titration with successively increased concentrations of an analyte (A) reacting with an immobilized ligand (B) to form a complex (AB) which gives rise to the detected SPR response. This titration is described in more detail in Example 1 below. Referring to the sensorgram, analyte concentration 80 nM was injected between 404-464 seconds, 240 nM between 523-583 seconds, 730 nM between 642-702 seconds, and 2200 nM between 760-820 seconds.

Before analysing the binding curve, start and end times for each injection of analyte are identified, and the base line is adjusted to zero level. Generally, the binding curve may then be analysed using an interaction model based on time dependent analyte concentration and allowing for mass transport limitation, such as the above-mentioned two-compartment model. If necessary, this model may be adapted to other interaction mechanisms, such as, e.g., conformation change (A+B $\leftrightarrow$ AB $\leftrightarrow$ AB*), competing reactions (A1+B $\leftrightarrow$ A1B; A2+B $\leftrightarrow$ A2B), parallel reactions (A+B1 $\leftrightarrow$ AB1; A+B2 $\leftrightarrow$ AB2), or bivalent analyte (A+B $\leftrightarrow$ AB; AB+B $\leftrightarrow$ AB2). Such models are described in more detail in, for example, the BIAevaluation Software Handbook mentioned above.

Assuming, for example, 1:1 binding, the following differential equation may represent the time dependent concentration of analyte A capable of binding to immobilized ligand B.

$$\frac{dA}{dt} = k_t(C_1 + C_2 + C_3 + \ldots C_n - A) - (k_a A * B - k_d AB) \quad (14)$$

where A is the surface concentration of free analyte A, $k_t$ is a transport coefficient, $C_1$ to $C_n$ are the different bulk concentrations of analyte, B is the concentration of immobilized ligand (ligand density), AB is the concentration of formed complex (=bound analyte), and $k_a$ and $k_d$ are the association rate constant and dissociation rate constant, respectively.

If at the beginning of the experiment the analyte concentration, A, at the surface is assumed to be zero, the concentration of ligand, B, is assumed to be $R_{max}$, and the concentration of formed complex, AB, is assumed to be zero, the following functions, here written in a form compatible with the above-mentioned BIAevaluation software, describe the interaction system.

AB+RI1*$1+RI2*$2+RI3*$3+RI4*$4+RI5*$5;
$1=(sign(t−tOn1)−(sign(t−tOff1))/2;
$2=(sign(t−tOn2)−(sign(t−tOff2))/2;
$3=(sign(t−tOn3)−(sign(t−tOff3))/2;
$4=(sign(t−tOn4)−(sign(t−tOff4))/2;
$5=kt*($1*conc1+$2*conc2+$3*conc3+$4*conc4−A);
$6=ka*A*B−kd*AB;
A=$5-$6|0;
B=−$6|Rmax;
AB=$6|0

In the above model, sign functions $1 to $4 (being 1 or 0) indicate when a certain analyte concentration is injected (tOn1 is the time when analyte concentration 1 is injected, tOff1 is the time when analyte concentration 1 is stopped, etc). Functions $5 and $6 describe together the variation of the surface concentration of analyte over time, $6 describing how the ligand density and complex varies with time. The function on the first line corresponds to the total change in signal from binding AB and bulk effects present during each injection. By numerical integration of these equations and global fitting to all data points of the whole sensorgram in FIG. 3, using, e.g., BIAevaluation software (Biacore AB, Uppsala, Sweden) adapted to the present invention, the kinetic rate constants $k_a$ and $k_d$ can be obtained. Mathematical models for the other interaction mechanisms may readily be devised by a person skilled in the art.

Figure 4:
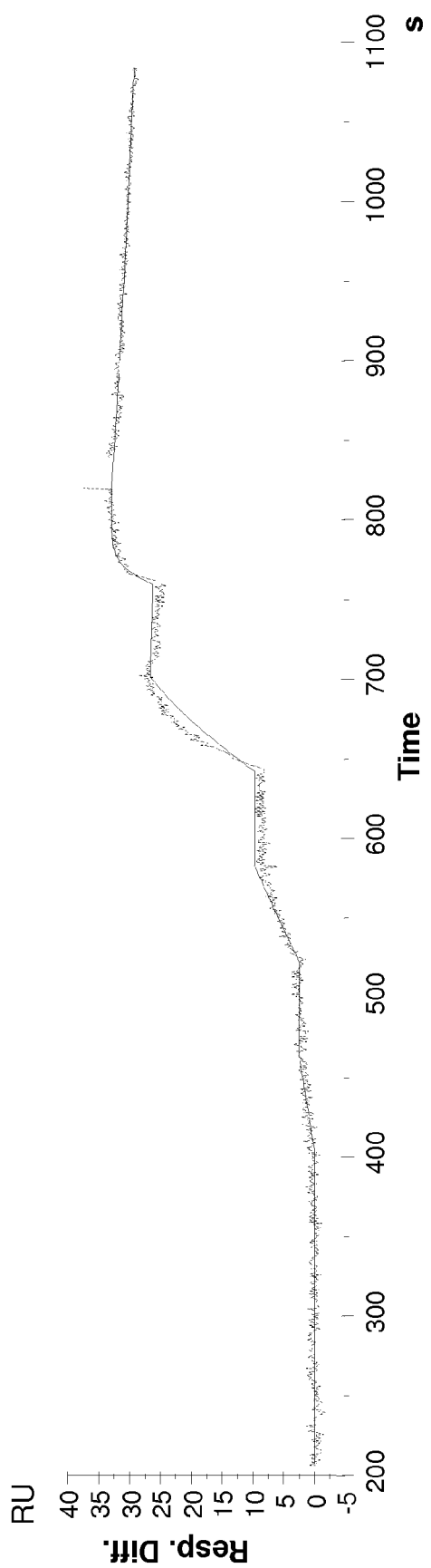
FIG. 4 is the sensorgram of FIG. 3 having overlaid thereon the binding curve resulting from global fitting.

The result of the fit is shown in FIG. 4, where the solid "non-rippling line" indicates the adapted curve for best fit for the concentration range 80-2200 nM, $k_a$ and $k_d$ being constrained to single values of $1.0*10^5$ $M^{-1}$ $s^{-1}$ and $6.6*10^{-4}$ $s^{-1}$, respectively, as described in Example 1 below.

With the above model, kinetic and affinity data can thus be obtained in spite of transport limitations. Since, as mentioned above, the method is insensitive to the injection order of analyte, analysis of relatively low analyte concentrations may be performed when binding is close to saturation or above the equilibrium response, thereby maximizing the kinetic information in the sensorgram where transport effects are small.

Data from binding analyses at two or more different ligand densities may advantageously be fitted simultaneously.

Measurement of concentration simultaneously with kinetic rate constants may be performed, using the above titration procedure and data fitting, provided that the transport coefficient $k_t$ is known and kept constant. Preferably, binding data from at least two, and preferably more ligand densities are then used.

A similar titration type approach as those described above may also be used to determine (at least approximate) kinetic rate constants for a plurality of different analytes binding to the same ligand (at the same or different known concentrations). In this case, different analytes are sequentially passed over the sensor surface rather than different analyte concentrations. The evaluation of the binding data is modified to permit fitting of different rate constants to the resulting total binding curve. Such a procedure may, for example, be used to screen different binding partners towards the ligand to quickly find the best binder, e.g., drug candidates binding to a drug target, such as a receptor. Optionally, this approach may be combined with the use of different analyte concentrations.

As mentioned above, analyte injections may also be performed by a "pulse injection" approach. An exemplary system for performing such a pulse injection method, based on the microfluidic system of a BIACORE® 3000 instrument (Biacore AB, Uppsala, Sweden), is schematically illustrated in FIG. 5.

Figure 5:
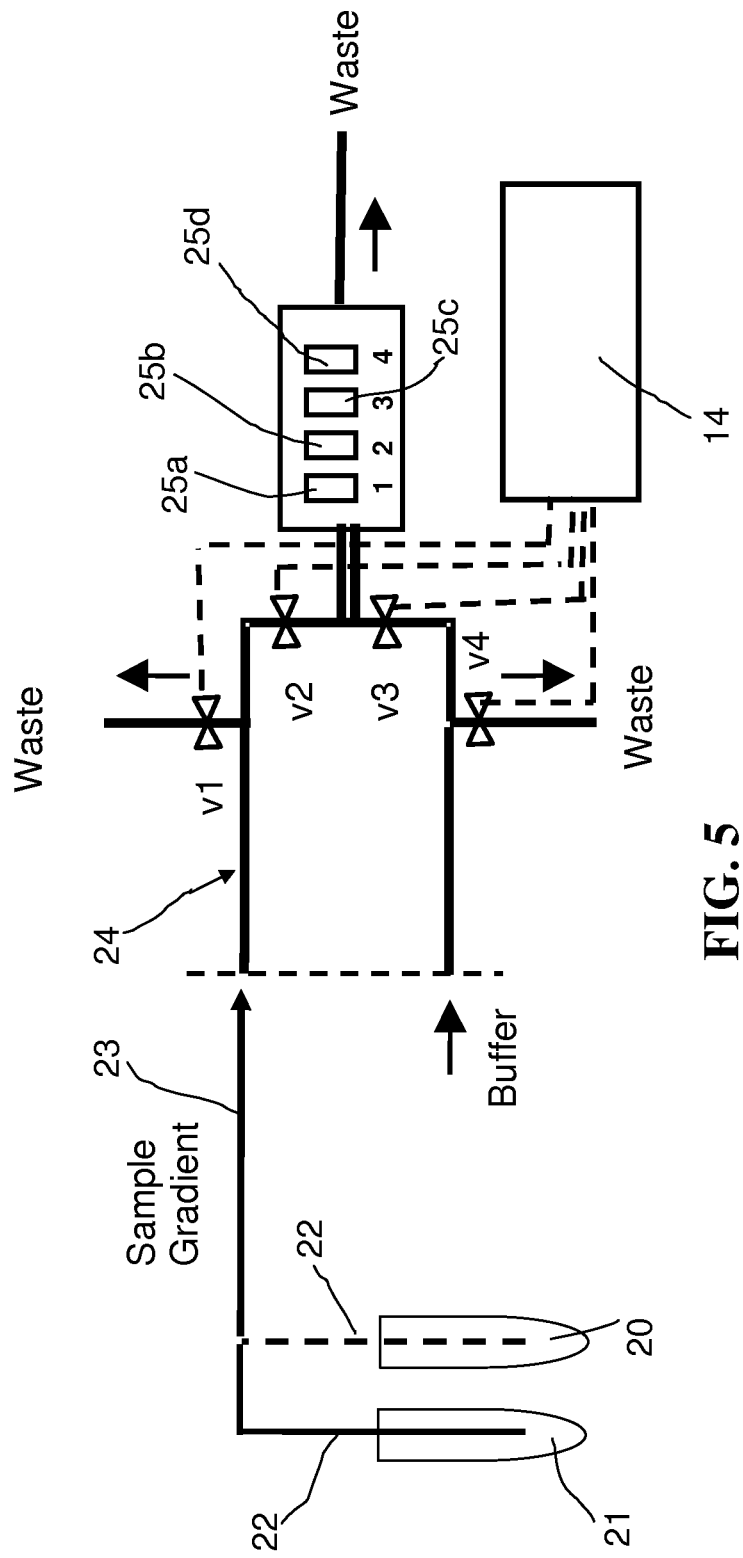
FIG. 5 is a schematic illustration of a system for creating a pulsed concentration gradient.

As can be seen in FIG. 5, there are provided two vessels (e.g., test tubes) 20 and 21 containing sample (20) and buffer (21), respectively. There is also provided a means 22 for aspirating liquid from the test tubes, indicated with vertical lines extending down into the test tubes. This means 22 can suitably be a needle, and since the same needle is used for both liquids, the needle shown in the sample tube 20 is shown by a broken line. The needle would thereby be physically moved between the tubes for the aspiration of liquids sequentially. Of course, there are other possibilities of devising the aspiration means, the one shown being only exemplary.

A system buffer supply is also provided. Initially the entire system is filled with buffer, i.e., all tubing contains this buffer. Respective segments of tubing 23 (sample and system buffer, respectively) are coupled to a microfluidic device 24 (in the BIACORE® instruments referred to as an Integrated Fluidic Cartridge—IFC) enabling controlled liquid delivery to one or more flow cells, in the illustrated case four flow cells 25a to 25d. Each flow cell has a sensor surface onto which one or more suitable target(s) are immobilized. There are also provided a number of valves v1 to v4 in the microfluidic device 24 for the control of the flows of the respective liquids. Valves v2 and v3 control the supply of fluid to the flow cells whereas valves v1 and v4 each are connected to waste. The valves v1 to v4 are controlled by a control unit 26. Alternatively, the flow in the various lines can be controlled by accurate pumps, whereby the actual flow rates can be monotonically controlled to provide the desired flow rates, ranging from zero flow to the maximum flow rates required, or combinations thereof.

The first step in the procedure is to aspirate a small volume of buffer into the needle 22, i.e., to immerse the needle into the buffer tube 21, and to aspirate the appropriate volume into the needle. It is however not strictly necessary to fill the needle with buffer by aspiration. Instead, the needle can be filled with buffer from the other end, i.e., from the system buffer supply by filling the entire system with buffer. Then, the needle is moved to the sample tube and a suitable volume of sample of about 500 μl is aspirated. However, the actual volume may depend on the application and the kind of sample, and can vary within wide limits, say between 1 μl and 4 ml.

The aspiration of sample will lead to mixing of the sample and buffer by dispersion, thereby creating a gradient in the tubing. In this case, the gradient will be a decreasing gradient (as seen from the needle) running through the tubing. If an increasing gradient is required, one would have to aspirate buffer after the sample aspiration, and ensure that a non-dispersed sample trailing edge is provided by first aspirating an air bubble to protect the sample from liquid already present in the needle, second a sample and third a buffer segment. The aspiration sequence always ends with aspiration of one or a few air bubbles to protect the gradient from liquid already present in the microfluidic device 24.

Prior to the first step, it is preferable to perform a few alternating air and sample aspirations to provide consecutive segments of air and sample and to inject them into the microfluidic device 24. In this way the sample will be protected from unwanted dispersion with running buffer in the microfluidic device, i.e., the leading front of the aspirated sample liquid will exhibit the nominal (maximum) concentration.

When a gradient has been established, it is injected via the needle into the microfluidic device and valves v2 and v3 in the sample and buffer flow lines are opened and closed according to a programmed sequence to enable alternating sample (exhibiting a gradient in the longitudinal direction of the tubing) and buffer pulses to be fed into the flow cells, such that the sample liquid flow is intersected at least once, preferably a plurality of times, by a further liquid, represented by the system buffer in this case. This intersection will create at least two separated segments of liquid. However, other further liquids than the system buffer are of course possible, such as pure solvent, solutions containing other species of interest, etc.

Thus, the leading edge of a decreasing sample gradient flow will represent a first concentration. Most often the concentration at the leading edge will be very close to the nominal, and can be taken to represent a known concentration. However, the major part of the sample flow will exhibit a gradient, and thus the majority of said segments that are created will have different concentrations with respect to the sample.

After a predetermined volume of sample gradient flow has passed into the flow cells, valve v2 is closed and valve v3 is opened, thereby injecting buffer into the line behind the sample flow. During the passage of analyte-containing sample over the sensor surface having targets immobilized on it, the analyte will associate with the targets. The volume of sample should preferably be sufficient to enable equilibrium to establish. However, it is not always required that equilibrium be reached but an equilibrium level can be calculated from the corresponding binding curve graph (response vs time). The time frames involved depend on sample specific binding and transport characteristics, flow rate, temperature, flow cell dimensions, etc.

When sample has been injected for a sufficiently long time, buffer is injected by opening valve v3 and closing valve v2. During the passage of buffer over the surface, analyte will dissociate. The process is repeated until the aspirated sample has been injected.

It is not necessary to inject the complete gradient into the flow cell. During buffer injection (v3 open, v2 closed) valve 1 can be opened to discard a small segment of the gradient. This will reduce the number of pulses produced and reduce the time needed for a full injection.

In an alternative embodiment, wherein a system without valves is used, during the association phase, i.e., during the time that the sample is passed through the sensor cell, the buffer flow is set to a very low value, less than 5%, and, e.g., about 1% of the regular flow. This is not strictly necessary, but prevents sample solution from leaking into the buffer line. Then a certain, predetermined amount of sample is injected into the microfluidic device at a specified rate. The buffer flow rate is then reset to the regular rate. During the passage of buffer through the cell, sample compound that has bound to the target on the sensor surface is allowed to dissociate for a suitable time period.

Figure 6:
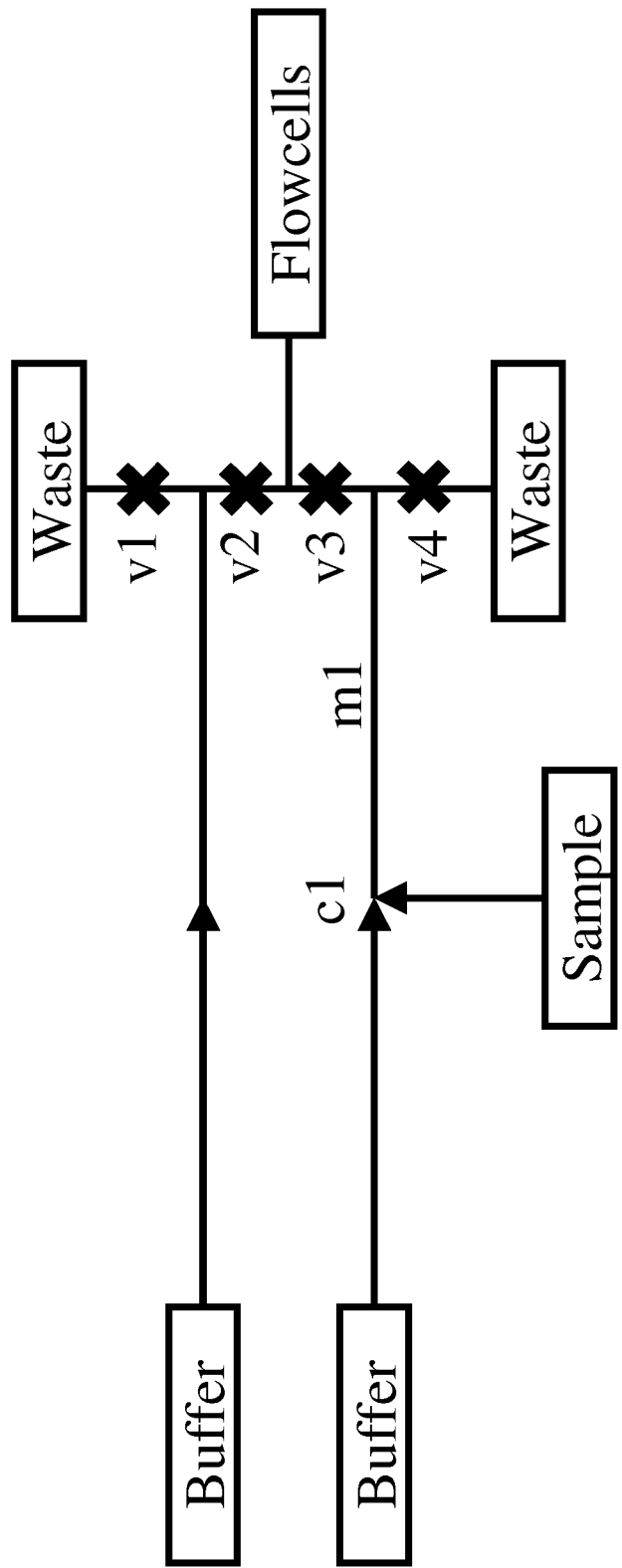
FIG. 6 is a schematic illustration of an alternative system for creating a pulsed concentration gradient.

In FIG. 6 there is shown an alternative method of creating a gradient using the microfludic device in FIG. 5. This is done by aspirating a sample segment of known concentration and diluting it with buffer in the microfluidic device using a connection c1 and a tubing segment m1. This allows the buffer and sample to form a homogenous mixture prior to contacting the flowcells. The pulses would be generated as previously described, i.e., by using alternating pumps or valves v2 and v3. The connection c1 could be a simple T-connection so that the concentration of the sample in the gradient is controlled by how the ratio of [flowrate (buffer)] and [flowrate (sample)] changes over time. Another possibility could be to have a two-way valve as connection c1. The concentration of the sample will be controlled by switching the inlet to m1 between buffer and sample, having the two-way valve open for buffer a different time than open for sample. In the tubing segment m1 the discrete connected segments of sample and buffer will form a homogenous mix due to dispersion. This method makes it possible to generate a gradient with known concentration of the sample at all times, in contrast to the dispersion concentration gradient where only the first few pulses have a known compound concentration. In the latter case, it will be necessary to fit the concentrations locally simultaneously as fitting the kinetic parameters. This will be described in more detail below.

While it currently is preferred to use so-called label-free detection methods, including those mentioned above, such as SPR, other detection techniques may, as already mentioned above, of course, also be contemplated, such as those based on the detection of a label, e.g., a radiolabel, fluorophore (including surface fluorescence), chromophore, chemiluminescer, a marker for scattering light, an electrochemically active marker, a thermoactive marker, etc.

The methods of the invention, including titration (i.e., sequential analyte injections) and evaluation with time dependent analyte concentration, are, as already mentioned above, suitably reduced to practice in the form of a computer system running software which implements the different steps of the procedure. Preferably, the titration is adaptive as mentioned above. The invention also extends to computer programs, particularly computer programs on or in a carrier, adapted for putting the titration procedure of the invention into practice. The carrier may be any entity or device capable of carrying the program. For example, the carrier may comprise a storage medium, such as a ROM, a CD ROM or a semiconductor ROM, or a magnetic recording medium, for example a floppy disc or a hard disk. The carrier may also be a transmissible carrier, such as an electrical or optical signal which may be conveyed via electrical or optical cable or by radio or other means. Alternatively, the carrier may be an integrated circuit in which the program is embedded.

Software like that outlined above may also be used to generate theoretical interaction curves for different interaction models similarly as described further above for the conventional single injection analysis procedures. By generating data for a complex model, for instance a conformation change model, varying parameters such as injection time and analyte concentration and then fitting this data to both a 1:1 binding model and a conformational change model, the residuals can identify conditions for optimal designs of kinetic experiments.

In the following Examples, various aspects of the present invention are disclosed more specifically for purposes of illustration and not limitation.

EXAMPLES

Instrumentation

A BIACORE® S51 instrument (Biacore AB, Uppsala, Sweden) was used in Examples 1 to 4 below. This instrument has two Y-type flow cells which allow a dual flow of fluids over a sensor chip surface, so-called hydrodynamic addressing, as described in, for example, EP-B1-1021703 (the disclosure of which is incorporated by reference herein). The instrument uses three parallel detection spots on the sensor chip.

A BIACORE® 3000 instrument (Biacore AB, Uppsala, Sweden) was used in Example 5 below. In this instrument, a micro-fluidic system passes samples and running buffer through four individually detected flow cells (one by one or in series).

As sensor chip was used Series S Sensor Chip CM5 (Biacore AB, Uppsala, Sweden) which has a gold-coated surface with a covalently linked carboxymethyl-modified dextran polymer hydrogel.

The outputs from the instruments via the instrument control software are "sensorgrams" which are a plots of detector response (measured in "resonance units", RU) as a function of time. An increase of 1000 RU corresponds to an increase of mass on the sensor surface of approximately 1 $ng/mm^2$. In Examples 1 to 4, evaluation was performed using BIAevaluation software, version 3.1 (Biacore AB, Uppsala, Sweden), adapted to a kinetic model as described above. In Example 5, evaluation was performed using BIAevaluation software, version 3.1 (Biacore AB, Uppsala, Sweden), Matlab version 5.3 (The MathWorks, Inc. Natick, Mass., U.S.A.) and Excel 97 (Microsoft Corp., Redmond, Wash., U.S.A.).

Example 1

Binding of a Kinase Inhibitor to Immobilized Kinase

Anti-histidine antibody (Qiagen 34660; Qiagen, Venlo, Netherlands) was diluted to 20 µg/ml in 10 mM acetate buffer pH 5.0, and 13000 RU of antibody was immobilized to a Series S Sensor Chip CM5 using amine coupling (Amine Coupling Kit—Biacore AB, Uppsala, Sweden) according to the manufacturer's instructions. The flow was 10 µl/min. Histidine tagged kinase (proprietary) was then captured and cross-linked to the sensor chip surface by injecting 30 µg/ml of the kinase in 10 mM PBS for three minutes followed by 2.5 min injections of EDC/NHS and ethanolamine to stabilise the kinase on the surface. With this procedure 4000 RU of kinase were immobilized.

A kinase inhibitor, staurosporin, was injected at concentrations of 80, 240, 730 and 2200 nM at a flow of 30 µl/min. The assay buffer was 50 mM Tris pH 7.5, 150 mM NaCl, 10 mM $MgCl_2$ and 3% DMSO. Overlay plots of observed and fitted data for the injection sequence are demonstrated in FIG. 3 (observed) and FIG. 4 (observed plus fitted). The association rate constant was calculated to $1.0*10^5$ $M^{-1}$ $s^{-1}$, and the dissociation rate constant $k_d$ to $6.6*10^{-4}$ $s^{-1}$.

Example 2

Figure 7:
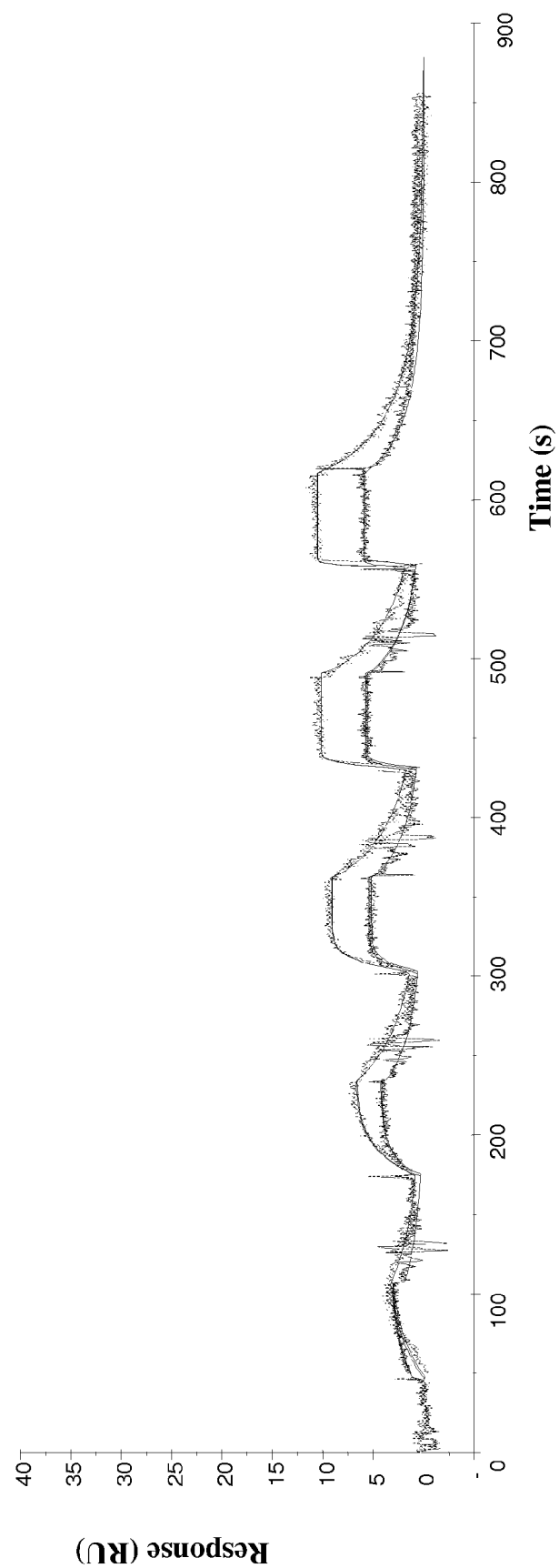
FIG. 7 is an overlay plot of observed and fitted binding data for sequential injections of a carbonic anhydrase inhibitor (acetazolemide) over a surface with immobilized carbonic anhydrase.
Figure 8:
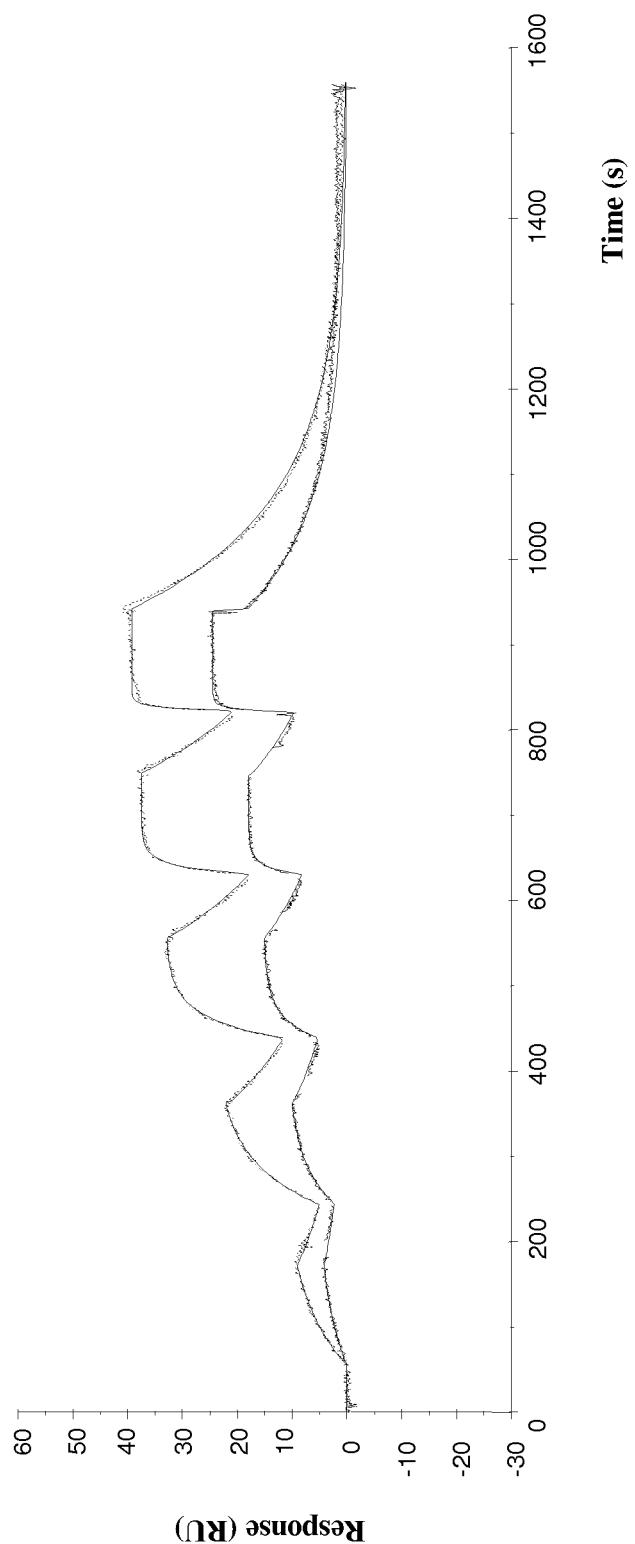
FIG. 8 is a similar overlay plot to that of FIG. 7 for sequential injections of another carbonic anhydrase inhibitor (azosulfamide).
Figure 9:
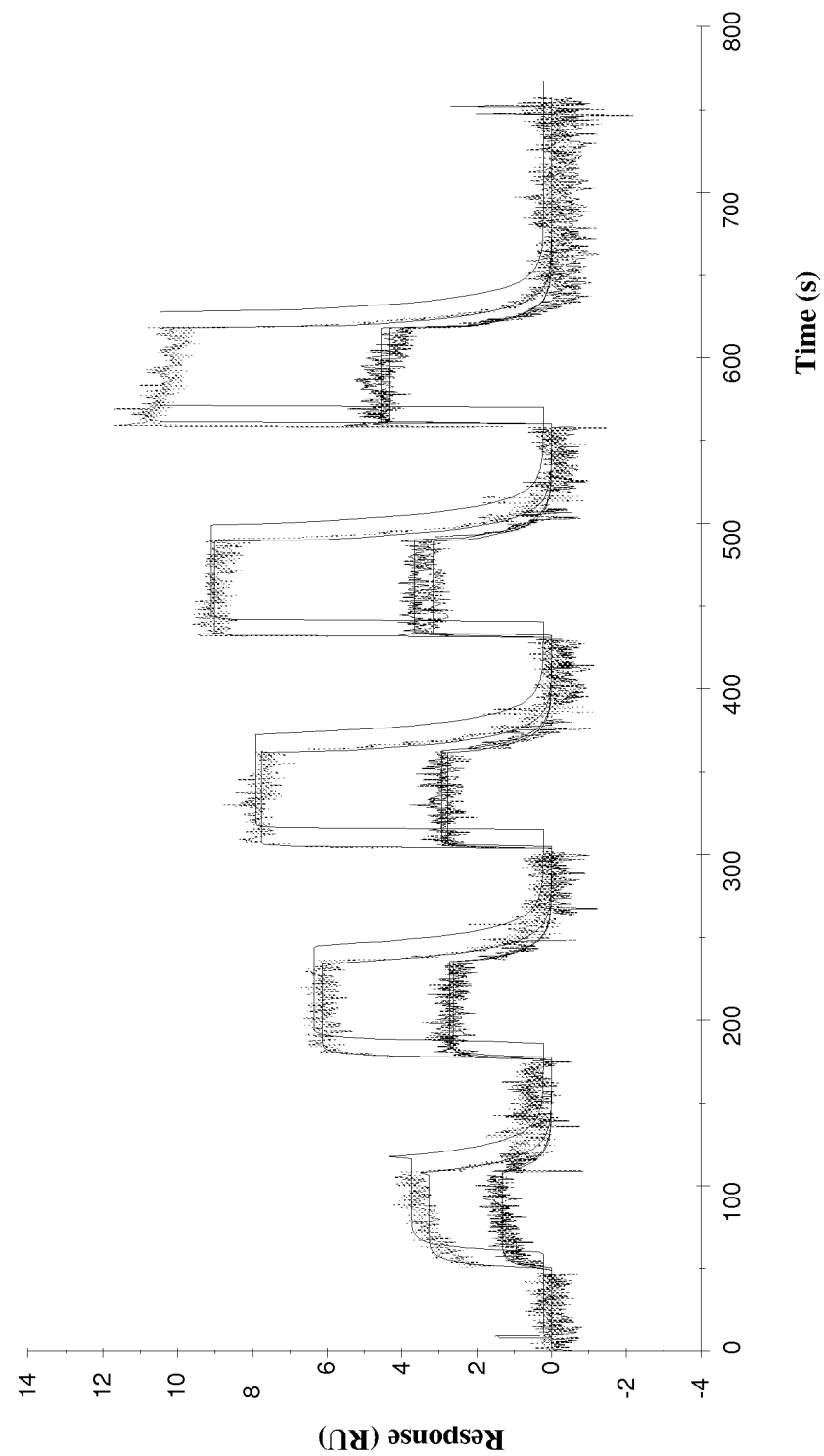
FIG. 9 is a similar overlay plot to those of FIGS. 7 and 8 for sequential injections of still another carbonic anhydrase inhibitor (benzenesulfonamide).

Binding of a Set of Carbonic Anhydrase Inhibitors to Immobilized Carbonic Anhydrase Carbonic anhydrase (Sigma C3640), 20 µg/ml in 10 mM acetate buffer pH 5.0, was immobilized to a Series S Sensor Chip CM5 using amine coupling according to the manufacturer's instructions (flow 10 µl/min), to obtain sensor surfaces with approximately 2000 and 700 RU, respectively, of immobilized carbonic anhydrase. Kinetic analysis was performed by injecting inhibitors in 10 mM PBS buffer with 0.005% P20 and 5% DMSO at a flow of 30 µl/min. The inhibitors were acetazoleamide (Sigma A6011), azosulfamide (Sigma A2759), and benzenesulfonamide (Aldrich 10,814-6). Overlay plots demonstrating observed and fitted data for the two ligand densities are presented in FIG. 7 (acetazoleamide), FIG. 8 (azosulfamide) and FIG. 9 (benzenesulfonamide). In FIG. 7, data represent two repeats on each ligand density, and $k_a$ was calculated to $1.8*10^6$ $M^{-1}$ $s^{-1}$, and $k_d$ to $4.0*10^{-2}$ $s^{-1}$. In FIG. 8, $k_a$ was calculated to $2.9*10^4$ $M^{-1}$ $s^{-1}$, and $k_d$ to $8.1*10^{-3}$ $s^{-1}$, and in FIG. 9 $k_a$ was calculated to $1.6*10^5$ $M^{-1}$ $s^{-1}$, and $k_d$ to $1.4*10^{-1}$ $s^{-1}$.

Example 3

Binding of a High Affinity Inhibitor to Immobilized Thrombin

Figure 10:
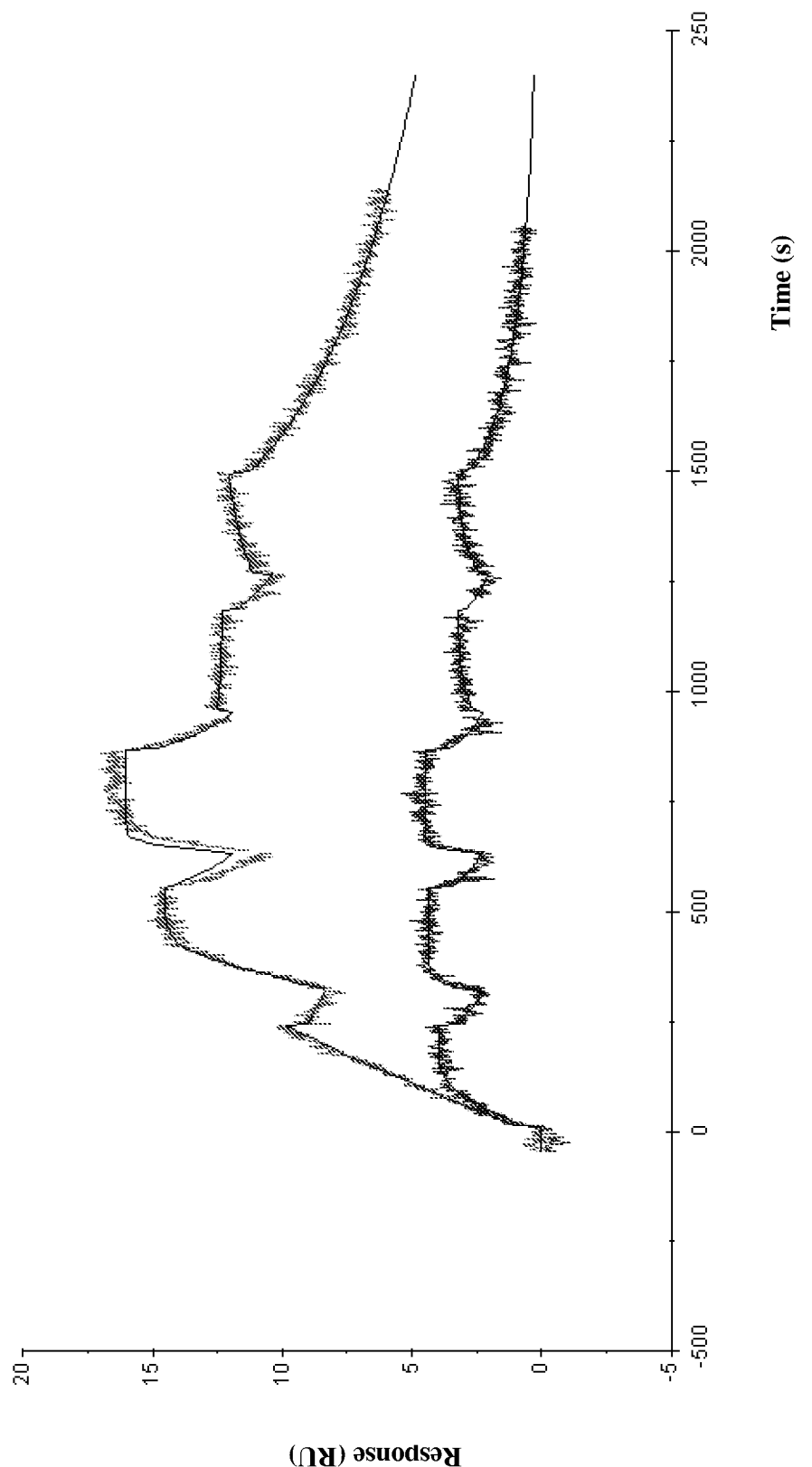
FIG. 10 is an overlay plot of observed and fitted binding data for sequential injections of a thrombin inhibitor (melagatran) over a surface with immobilized thrombin.

Thrombin (Sigma T 1063), 20 µg/ml in 10 mM acetate buffer pH 5.0, was immobilized to a Series S Sensor Chip CM5 using amine coupling according to the manufacturer's instructions (flow 10 µl/min), resulting in sensor surfaces with approximately 2300 and 600 RU, respectively, of immobilized thrombin. Kinetic analysis was performed by injecting a high affinity thrombin inhibitor, melagatran (a gift from Johanna Deinum, AstraZeneca, Mölndal, Sweden), in 10 mM PBS buffer with 0.005% P20, 5% DMSO and 3.4 mM EDTA at a flow of 30 μl/min. Overlay plots demonstrating observed and fitted data are presented in FIG. 10. The calculated $k_a$ was $2.0*10^7$ $M^{-1}$ $s^{-1}$, and $k_d$ $1.8*10^{-2}$ $s^{-1}$.

Examples 1 to 3 above demonstrate that a wide range of rate constants can be determined with the sequential injection procedure. In these Examples $k_a$ values range from $2.9*10^4$ to $2.0*10^7$ $M^{-1}$ $s^{-1}$ and $k_d$ values range from 0.14 to 6.6 $10^{-4}$ $s^{-1}$. The Examples also illustrate that kinetic data can be obtained using one or two ligand densities and that the injection order can be mixed and not only in the order from low to high concentration.

Example 4

Combined Sequential and Single Injections

Figure 11:
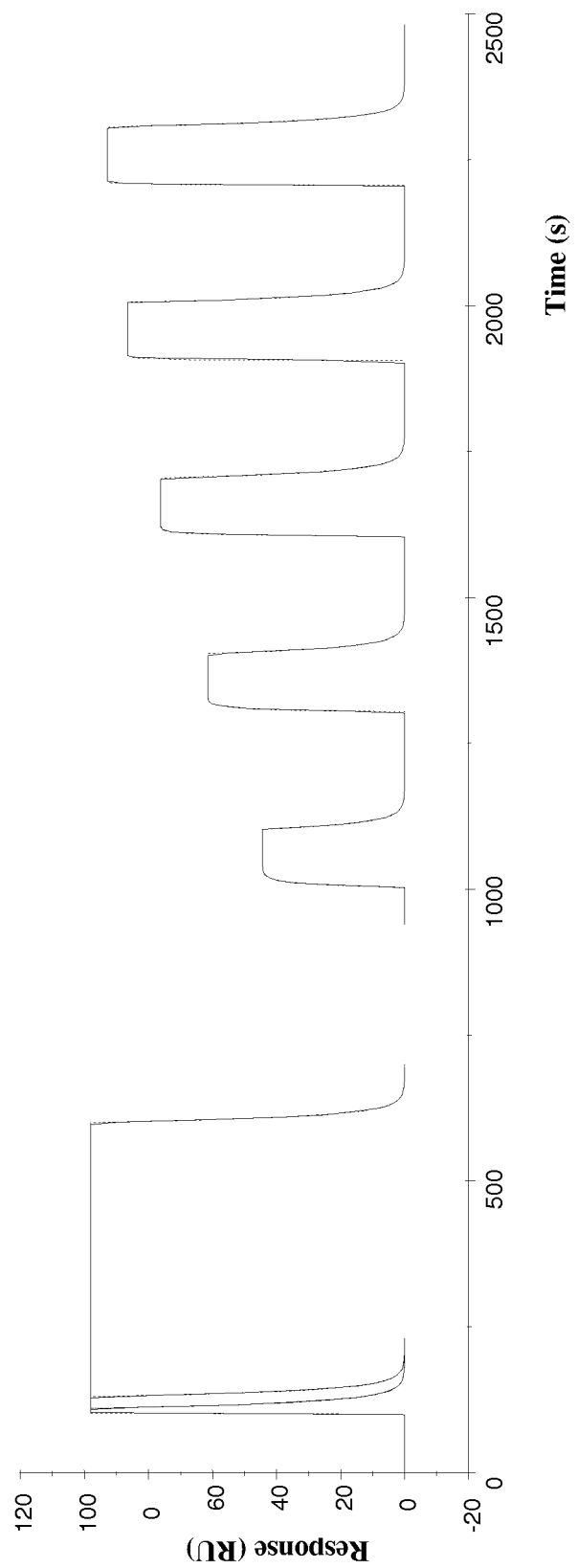
FIG. 11 is an overlay plot of four binding curves and fitted data, three curves (to the left) representing sensorgrams with single injections of analyte, and one curve (to the right) representing a sensorgram for sequential injections of analyte.

In FIG. 11, simulated data representing sequential and single injections are combined in the evaluation where all binding curves are fitted simultaneously. The figure shows an overlay plot of four binding curves and fitted data. The three curves to the left represent sensorgrams with single injections of analyte at 51200 nM but with varying injection times, 10 s, 30 s and 500 s, whereas the curve to the right represents sequential injections of analyte from 800 to 12800 nM. This illustrates that sensorgrams with varying numbers of injections and injection times can be analysed.

Example 5

Estimation of Interaction Rate Constants

Figure 12:
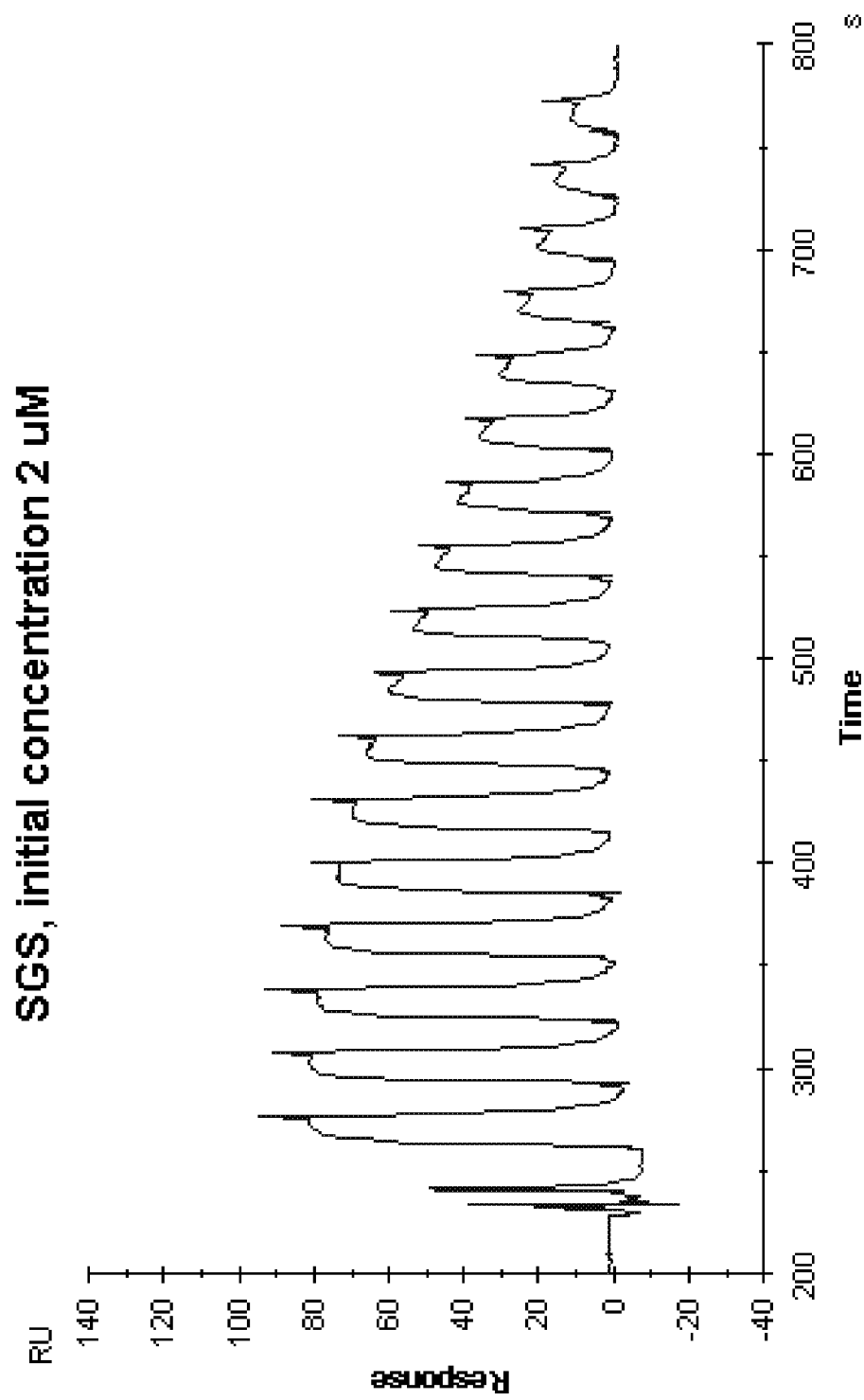
FIG. 12 is a sensorgram obtained by pulse injection of camel antibody (SGS) over a surface with immobilized lysozyme.

The kinetics of a camel derived heavy chain triple mutant single domain antibody (cAb-Lys3:s SGS) binding to lysozyme (obtained from the Department of Ultrastructure, Vrije Universiteit, Brussels, Belgium) was studied with the "pulse injection method" described above. All experiments were performed at 30° C. 190 RU (chip 1) and 280 RU (chip 2) of lysozyme was immobilized using a standard amine coupling procedure. Upon a 2-min activation, lysozyme (8 μg/ml in 10 mM $Na_2HPO_4$, pH 7.0) was injected for 3 min (chip 1) and 4 min 30 s (chip 2). 10 mM $Na_2HPO_4$, pH 7.0 (flow rate 5 μl/min) was used as running buffer during immobilization. SGS was injected at different initial concentrations (0.5, 1.0 and 2.0 μM in HBS-EP). The results are shown in FIG. 12.

Bulk errors in the sample solutions were corrected for by subtraction of the reference flow cell signals. Individual pulses were separated and aligned, using MATLAB, so that each pulse corresponded to one binding curve. The curves were superimposed in the BIAevaluation software. 15 pulses were used in every fit. The first two pulses were assumed to be of initial concentration. Global starting values of $k_a$, $k_d$ and $R_{max}$ were fitted to the second pulse (pulse number one was omitted because of its irregular shape), since its concentration was known. These values were then used to locally fit the concentrations of all pulses. $k_a$, $k_d$ and $R_{max}$ estimations were refined, using the new concentration information. The process was repeated until all parameters converged. Each pulse injection was evaluated separately. The fitting of the concentration resulted in a partially linear concentration gradient. Kinetic data obtained with the pulse injection method is presented together with mean values and standard deviations in Table 1 below.

TABLE 1

Results from a pulse injection assay with camel antibody SGS and lysozyme

| | $C_0$(μM)* | $k_a$ ($M^{-1}s^{-1}$) | $k_d$ ($s^{-1}$) | $R_{max}$ (RU) | $K_D$ (M) | $\chi^2$** |
|---|---|---|---|---|---|---|
| Chip 1 | 0.5 | 1.75e5 | 0.508 | 137 | 2.9e−6 | 0.0972 |
| (190 RU) | 0.5 | 9.99e4 | 0.435 | 180 | 4.35e−6 | 0.151 |
| | 0.5 | 1.17e5 | 0.484 | 170 | 4.14e−6 | 0.122 |
| | 1 | 1.91e5 | 0.475 | 112 | 2.5e−6 | 0.243 |
| | 1 | 4.6e5 | 0.514 | 72.7 | 1.12e−6 | 0.198 |
| | 1 | 1.62e5 | 0.513 | 126 | 3.17e−6 | 0.325 |
| Chip 2 | 1 | 4.60e5 | 0.466 | 119 | 1.01e−6 | 0.383 |
| (280 RU) | 1 | 1.11e5 | 0.462 | 286 | 4.15e−6 | 0.374 |
| | 1 | 1.32e5 | 0.42 | 251 | 3.19e−6 | 0.348 |
| | 2 | 1.87e5 | 0.487 | 188 | 2.60e−6 | 1.53 |
| | 2 | 2.41e5 | 0.464 | 151 | 1.93e−6 | 0.816 |
| | 2 | 2.79e5 | 0.421 | 137 | 1.51e−6 | 1.85 |
| Average: | | 2.18e5 | 0.471 | 133 189 | 2.71e−6 | |
| St. dev: | | 1.25e5 | 0.033 | 39.3 66.8 | 1.16e−6 | |
| Rel. st. dev.: | | 57% | 7% | 30% 35% | 43% | |

*$C_0$ is the nominal concentration of SGS
**$\chi^2$ is a statistical measure of the quality of the fit It is to be understood that the invention is not limited to the particular embodiments of the invention described above, but the scope of the invention will be established by the appended claims.

The invention claimed is:

1. An analytical system for monitoring interactions between molecules comprising:
   an interaction detector for detecting a reversible molecular interaction between a ligand immobilized to a solid support surface and a binding partner to the ligand in a fluid flow; and
   a microfluidic system arranged to provide a fluid flow to the interaction detector with known concentration of the binding partner comprising:
     a sample solution inlet;
     a buffer solution inlet;
     a tubing segment connecting the sample solution inlet and the buffer solution inlet to the interaction detector;

a pump or a valve arranged to control supply of sample solution and buffer solution into each one of the sample solution inlet and the buffer solution inlet respectively; and a controller for controlling the operation of said pumps or valves to provide a supply of sample solution and buffer solution into the tubing segment to dilute the sample solution to form a homogenous mixture of buffer and sample solution with a known concentration of the binding partner at the interaction detector, wherein the controller is arranged to control the operation of said pumps or valves to sequentially, without intermediate regeneration or renewal of the immobilized ligand, flow from said tubing segment a plurality of fluid volumes containing different known concentrations of the sample solution over the interaction detector during a same analytical cycle to permit association of the binding partner in the sample solution to the ligand immobilized to the solid support surface of the interaction detector, and wherein the controller is further arranged to:
  a) monitor the momentary amount of binding partner bound to the solid support surface of the interaction detector as a function of time and sample solution concentration,
  b) collect binding data, and
  c) determine kinetic parameters by globally fitting a predetermined binding interaction model for the interaction between the binding partner and the immobilized ligand to the collected binding data.

2. The analytical system of claim 1, wherein the controller is arranged to control the operation of said pumps or valves to provide a supply of sample solution and buffer solution create a stepwise gradient of known concentrations of the binding partner at the interaction detector.

3. The analytical system of claim 1, wherein the solid support surface is a sensor surface.

4. The analytical system of claim 1, wherein the detection at the solid support surface is based on evanescent wave sensing.

5. The analytical system of claim 1, wherein the detection at the solid support surface is based on surface plasmon resonance (SPR).

6. The analytical system of claim 1, wherein the detection at the solid support surface is based on detection of a label.

7. The analytical system of claim 1, wherein the sample solution inlet and the buffer solution inlet each is connected to the tubing segment by a pump controlled by the controller.

8. The analytical system of claim 1, wherein the sample solution inlet and the buffer solution inlet are connected to the tubing segment by a two-way valve controlled by the controller.

9. The analytical system of claim 2, wherein the controller is arranged to control the operation of said pumps or valves to sequentially, flowing from said tubing segment a plurality of fluid volumes containing different known concentrations of the sample solution over the interaction detector to permit association of a binding partner in the sample solution to a ligand immobilized to a solid support surface of the interaction detector wherein the controller is further arranged to:
  a) monitor the momentary amount of binding partner bound to the solid support surface of the interaction detector related to time and sample solution concentration of binding partner and collecting the binding data; and
  b) determine the kinetic parameters by globally fitting a predetermined binding interaction model for the interaction between the binding partner and the immobilized ligand to the collected binding data.

* * * * *